Jan. 15, 1952 E. S. BOERNER Plant Pat. 1,065
ROSE PLANT
Filed Nov. 28, 1950
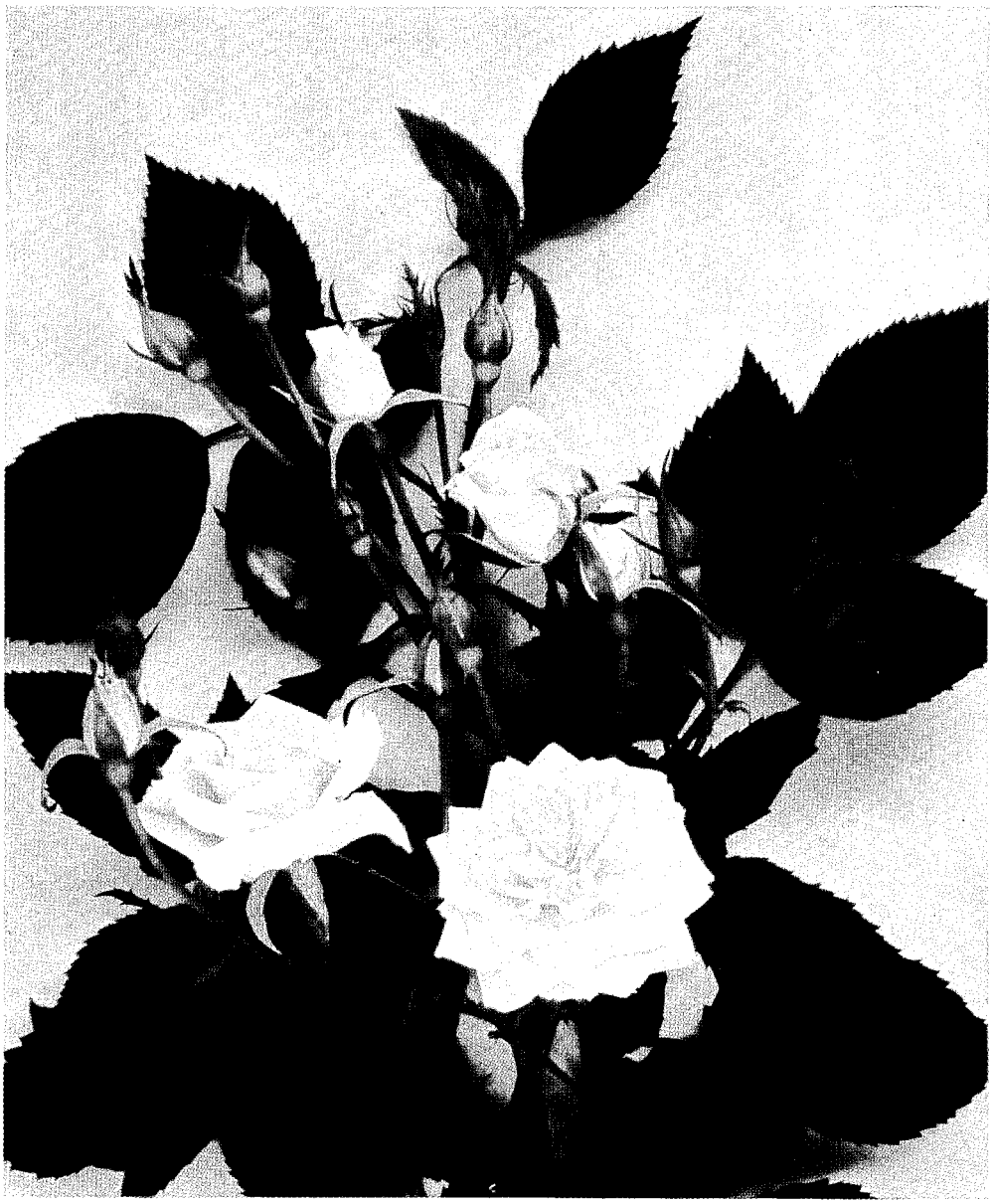
Inventor.
E. S. Boerner
By: Robert Cobb
Attorneys.

Patented Jan. 15, 1952

Plant Pat. 1,065

UNITED STATES PATENT OFFICE 1,065

ROSE PLANT

Eugene S. Boerner, Newark, N. Y., assignor to Jackson & Perkins Company, Newark, N. Y., a corporation of New York Application November 28, 1950, Serial No. 197,897

1 Claim. (Cl. 47—61)

The present invention relates to a new and distinct variety of rose plant of the floribunda class, originated by crossing the variety "Garnette" (unpatented) with an unnamed, unpatented yellow seedling.

The primary objective in making this cross was to obtain a rose of the "Garnette" type in a new color of flower, but retaining the lasting quality, stiff petals and good production which are characteristic of this parent.

This objective was fully achieved, as evidenced by the following features which are distinctive in the new variety and distinguish it from both parents, as well as from all other known varieties of which I am aware:

(1) The Cameo Pink color of the flowers;

(2) The long-lasting quality of the flowers, both on the plant and as cut-flowers;

(3) The prolific production of flowers when grown in the greenhouse; and (4) The hardiness when grown out-of-doors.

Asexual reproduction of the new variety by budding at Newark, New York, and at Pleasanton, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with the Ridgway's Color Standards and Nomenclature:

Parentage: Seedling.

*Seed parent.*—"Garnette."

*Pollen parent.*—An unnamed yellow seedling.

Classification:

*Botanic.*—Large-flowered polyantha.

*Commercial.*—Floribunda.

*Flower*

(Observations made in the greenhouse at Newark, New York, in the early morning in the month of May, 1950.)

Blooming habit: Recurrent—continuous.

Bud:

*Size.*—Medium.

*Form.*—Ovoid. Is not affected by wet or hot weather.

*Color.*—When sepals first divide—Rose Pink, Plate 12. When petals begin to unfurl—Rosolane Pink, Plate 26. When half blown—inside of petals—Cameo Pink, Plate 26; reverse of petals—Cameo Pink, Plate 26, lightly overcast with White, Plate 53, on the lower half of the petal.

*Sepals.*—Color—inside—Biscay Green, Plate 17; outside—Light Bice Green, Plate 17. Serrated; curl back when petals begin to unfurl.

*Calyx.*—Color—Biscay Green, Plate 17. Shape—funnel. Size—small. Aspect—smooth. Odor when rubbed—none.

*Peduncle.*—Length—short. Aspect—rough. Color—Biscay Green, Plate 17. Strength—erect; slender.

*Opening.*—Opens up well. Is not affected by adverse weather conditions.

Bloom:

*Size.*—Medium. Average size when fully expanded—2 to 2½ inches.

*Borne.*—Singly and in irregular clusters.

*Stems.*—Medium length; strong.

*Form.*—When first open—cupped. Permanence—flattens.

*Petalage.*—Very double (many petals and stamens hidden). Number of petals under normal conditions—45 to 50.

*Color.*—Center of flower—Cameo Pink, Plate 26. Outer petals—White, Plate 53, lightly overcast with Cameo Pink, Plate 26. Base of petals (aiglet)—Pale Chalcedony Yellow, Plate 17. Inside of petals—Cameo Pink, Plate 26. Reverse of petals—White, Plate 53, lightly overcast with Cameo Pink, Plate 26. General tonality from a distance—Cameo Pink, Plate 26.

*Discoloration.*—General tonality at end of first day—Cameo Pink, Plate 26. Second day—Cameo Pink, Plate 26. Third day—White, Plate 53, lightly overcast with Cameo Pink, Plate 26.

Petals:

*Texture.*—Leathery. Is not affected by wet or hot weather.

*Appearance.*—Inside—satiny. Outside—shiny.

*Form.*—Oval.

*Arrangement.*—Irregular. Petaloids in center—few; small.

*Persistence.*—Drop off cleanly.

*Fragrance.*—Moderate. Nature—tea (average hybrid tea scent).

*Lasting quality.*—On the plant and as cut flower—very long.

Genital organs:

*Stamens, anthers.*—Medium size; few. Color—Ochraceous-buff, Plate 15. Arrangement—regular around styles.

*Stamens, filaments.*—Short. Color—Sulphur Yellow, Plate 5.

*Pollen.*—Color—Martius Yellow, Plate 4.
*Styles.*—Loosely separated; uneven length; short; thin.
*Stigmas.*—Color—Light Dull Green Yellow, Plate 17.
*Ovaries.*—All enclosed in calyx.

*Plant*

Form: Bush.
Growth: Vigorous; branching.
Foliage: 3 to 5 leaflets.
*Size.*—Medium.
*Quantity.*—Abundant.
*Color.*—New foliage—upper side: Victoria Lake, Plate 1; under side: Oxblood Red, Plate 1. Old foliage—upper side: Forest Green, Plate 17; under side: Light Elm Green, Plate 17.
*Shape.*—Oval pointed.
*Texture.*—Upper side—leathery. Under side—smooth. Ribs and veins—ordinary.
*Edge.*—Serrated (saw toothed).
*Serration.*—Double; sharp.
*Leaf stem.*—Color—Absinthe Green, Plate 31. Under side—prickles.
*Stipules.*—Medium length; bearded.
*Disease resistance.*—Resistant.

Wood:
*New wood.*—Color—Hay's Russet, Plate 14. Bark—smooth.
*Old wood.*—Color—Cress Green, Plate 31. Bark—smooth.
Thorns:
*Thorns.*—Quantity—on main stalks from base—few; on laterals from stalk—none. Form—narrow base; short; straight. Color when young—Light Yellowish Olive, Plate 30. Position—irregular.
*Prickles and short needles.*—None.

I claim:

A new and distinct variety of rose plant of the floribunda class, characterized as to novelty by the Cameo Pink color of its flowers, by the long-lasting quality of the flowers both on the bush and as cut-flowers, by its prolific flower production when grown in the greenhouse, and by its hardiness when grown out-of-doors, substantially as shown and described herein.

EUGENE S. BOERNER.

No references cited.